United States Patent [19]
Rocha-Sosa et al.

[11] Patent Number: 5,436,393
[45] Date of Patent: Jul. 25, 1995

[54] POTATO TUBER SPECIFIC TRANSCRIPTIONAL REGULATION

[75] Inventors: Mario Rocha-Sosa, Cuernavaca, Mexico; Uwe Sonnewald, Berlin, Germany; Wolf-Bernd Frommer, Berlin, Germany; Lothar Willmitzer, Berlin, Germany; Marina Stratmann, Berlin, Germany

[73] Assignee: Institut für Genbiologische, Germany

[21] Appl. No.: 995,911

[22] Filed: Dec. 22, 1992

Related U.S. Application Data

[63] Continuation of Ser. No. 454,363, Dec. 21, 1989, abandoned.

[30] Foreign Application Priority Data

Dec. 21, 1988 [DE] Germany .................. 38 43 627.2

[51] Int. Cl.$^6$ .............. A01H 1/04; C12N 15/00; C12N 5/00; C07H 21/04
[52] U.S. Cl. .............. 800/205; 800/DIG. 42; 435/172.3; 435/240.4; 536/24.1
[58] Field of Search ............... 435/69.1, 70.1, 172.3, 435/240.4, 252.2, 252.3, 320.1; 536/24.1; 800/205, DIG. 42, DIG. 43

[56] References Cited

PUBLICATIONS

Wenzler et al. 1989. Plant Mol. Biol. 12(1):41–50.
Larkins et al. 1985. J. Cell. Biochem. Suppl. 9C:264.
Murai et al. 1983. Science 222:476–482.
Bevan et al. 1986. Nucleic Acids Research 14(11): 4625–4638.
Twell et al. 1987. Plant Mol. Biol. 9:365–375.
Bevan et al. 1988. Heredity 61(2): 280.
Bevan et al. 1986. Nucleic Acids Research 14(11): 4625–4638.
Mignery et al. 1988. Gene 62:27–44.
Jaynes et al. 1986. Trends in Biotechnol. 4(12): 314–320.
Plant Molecular Biology 9:365–375 (1987) Twell et al.
"The 5' Flanking DNA of a patatin gene directs tuber specific expression of a chimaeric gene potato".
(Two Hundred and EightMeeting of the Genetical Society) Heredity 61(2) (1988) Bevan et al. "Transcriptional regulation of genes during potato tuberization" p. 280.
Journal of Cellular Biochemistry, Supp. 12C:206 (1988) "Molecular Analysis of The Patatin Gene Family of Potato (Solanum Tuberosum L.)" Twell et al.
Journal of Cellular Biochemistry, Supp. 12C:199 (1988) "Expression of foreign genes in solanum tuberosum CVS bintje and desiree" Lawton et al.
Journal of Cellular Biochemistry, Supp 11B:57 (1987) "Regulated Expression of a Chimeric Patatin—Glucuronidase Fusion in Tubers and Induced Internode Cuttings of Transformed Potato" Jefferson et al.
Embo Journal, 8:23–29 (1889) "Both developmental and metabolic signals activate the promoter of a class 1 patatin gene" Sosa et al.
Trends Biotechnol 4:314–320 (1986) "Plant protein improvement by genetic engineering: use of synthetic genes" Jaynes et al.
Gene, 62:27–44 (1988) "Molecular characterization of the patatin multigene family of potato" Mignery et al.

*Primary Examiner*—David T. Fox
*Attorney, Agent, or Firm*—Ostrolenk, Faber, Gerb & Soffen

[57] ABSTRACT

There is described a new DNA sequence of an expression cassette on which the potato tuber specific regulatory regions are localised as well as the transfer of this DNA sequence into the plant genome using agrobacteria as transfer micro-organisms. The DNA sequence contains a patatin gene with a patatin gene promoter. The transfer DNA sequence acts both for regulating endogenous as well as for preparation of heterologous products in crops.

7 Claims, 3 Drawing Sheets

```
       AAGCTTATCTTGCCATATAGAGTAGTTTGTGATGGTATACTTCATAAACTTTAACTTATGTTAAATTGTAATGATAAATTTTATTGTAAATTAAAA
       ATTACTTATAAAATTGGGCATTATAACATATGAAAGACAAATTGTCTTACATATTTTACTTTTGACTTTAATATGAATATTTCAATTTAAATCATTGTTT
-1500  TATTTTCTCTTTCTTTTTACAGGTATAAAAGGTGAAAATTGAAGCAAGATTGTCAAGCTATGTGCCAAGCTATGATACTTTGATACTTTGAAGAAATTTT
       TACTTATATGTCTTTGTTTAGGACTGAATATATTGATATGTTTTAGTGTATCATTTCTTGTCATTTATGCTTTAGTGTATAATTTAGTATATTTATATGA
       TCATGGGTGCAATTTTGATACAAATATTTTTGTCATTAAATAAATTATCACAACTGTCATTACTTTCAGTGACAAAAATGTATTGTCGTAGTACCC
       TTTTTGTTGAATATGAATAATTTTTATTTGTGACAATGTAATTGTCACTACTTATGATAATATTAGTGACATATGTCGTCGGTAAAGCAA
       ACACTTCAGTGACAAAATAATAGATTAATCACAAATTAATCAAAATTATTAACCTTTTTATAATAAAATTTATCCTAATTTATACATTTAAGGACAAAGTATT
-1000  TTTTTATATATAAAAATAGTCTTTAGTGACGATCGTAGTGTTGAGTCTAGAAATCATAATGTTGAATCTAGAAAATCTCATGCAGTCTAAAATAAAC
       CTCAAAAGGACGTTCAGTCCATAGAGGGGGTCTATGTGACACCCCAACCTCAGCAAAGAAAACCTCAACAAGGACATTTGCGGTGCTAAACAA
       TTTCAAGTCTCATCACACATATATTATTATATAATACTAATAAAGAATAAAGGTAAACATCATTAAATCGTCTTTGTATATTTTAGTGAC
       AACTGATTGACGAAATCTTTTTCGTCACACAAATTTTTAGTGACGAAACATGATTTATAGATGATGAAATTATTGTCCCTCATAATCTAATTTGTGT
       AGTGATCATTACTCCTTTGTCTTTATTTGTCATGTTAGTCCATTAAAAAAATATCTCTCTTCTTATGTACCGTGAATGGTGGAACGGATCTATTA
-500   TATAATACTAATAAAGAATAGAAAAAGGAAAGTCAGTGAGTTCGAGGGAGAGAATCTGTTTAATATCAGAGTCGATCATCGTGTCAATTTATCGATATG
       ACCCTAACTTCAACTGAGTTAACCAATTCCGATAAGGCGAGAAATATCATGTATTGAGTCTAGAAAAATCTCATGTAGTGTGGGTAAACCTCAGCAA
       GGACGTTGACTCCATAGAGGGGGGTGTATGTGACACCCCAAGCTCAACACCTCAGCAAAGAAAACCTCCCCTCAAGAAGGACATTTGCGGTGCTAAACATTTCAAG
       TCTCATCACACATATATATATATATATATAACTAACTAACGACAGTTGCGGTGCCAAACTGAGTGAGGT
-100   AATAAACATCACTAACTTTTATTGGTTATGTCAAACTCAAGTAAATTTCTCAACTTGTTACGTGCCTATATACCATGCTGTTATATGCTCAAAG
       CACCAACAAATTTAAAACACTTTGAACATTTGCAAATGGCAACTACTAAACTTTTAATTTTATGATATTAGCAACTACTAGTTCAAC
       ATGTGCTAAGTTGGAAGAAATGCTTACTCTTCTAAGTATTGATGGAGGTGGAATTAAGGAATCATTCCAGTATCATTCCAGTCATTCTGGGTACCT
       CTTCAGGTATTGTAAAATATTTTTAATGTATGTGCCTAAGTGTGACACTACTATAGTCATTCTGAAGGACAA
```

FIG. 2

POTATO TUBER SPECIFIC TRANSCRIPTIONAL REGULATION

This is a continuation of application Ser. No. 07/454,363 filed on Dec. 21, 1989, now abandoned.

SUMMARY OF THE INVENTION

This invention relates to a new DNA sequence of an expression cassette on which the potato tuber specific regulatory regions are localised as well as the transfer of this DNA sequence into a plant genome using agrobacteria as the transfer micro-organisms. The DNA sequence contains a patatin gene with a patatin gene promoter. The transfer DNA sequence acts both for regulating endogenous as well as for the preparation of heterologous products in crops.

BACKGROUND OF THE INVENTION

Because of the continual increasing need for food and raw materials due to the growth in world population, and because of the long-term reduction in areas of land suitable for growing crops, it is becoming increasingly the task for biological research to increase the yields of crops and their food content. An increase of yields can be achieved among other methods by increasing the resistance of crops against plant pests and plant diseases and/or poor soils. An increase of the resistance could be achieved for example in such a way that the plants induce and give rise to an increased formation of protective substances. For this, the metabolism of the plants must be manipulated. This can be achieved among other ways by changing the DNA contained in the cell nuclei. It would be desirable to act on those sequence of DNA which are responsible for transcription in one or more of the parts of the plant or during a specified period in the plant growth cycle. For this reason there is great interest in identifying the DNA sequences in the plant genome responsible for the transcription or expression of endogenous plant products. In order to find such DNA sequences, products first have to be sought which appear at a specific time in the cell growth cycle or in a specific part of the plant. If the desired gene is to be identified and isolated, a careful investigation of the sequence, and above all the identification and isolation of the desired transcriptional regulatory regions, is necessary. Suitable models must then be provided whose functions must be established through experiments. Identifying such DNA sequences is a challenging project which is subject to substantial pitfalls and uncertainty. There is however substantial interest in the possibility of genetically modifying plants, which justifies the substantial expenditure and efforts necessary in identifying transcriptional sequences and manipulating them to determine their utility. Processes for genetic modification of dicotyledonous and monocotyledonous plants are known (EP 267159), as well as the following publications of Crouch et al., in: Molecular Form and Function of the Plant Genome, eds. van Vloten-Doting, Groots and Hall, Plenum Publishing Corp, 1985, pp 555-566; Crouch and Sussex, Planta (1981) 153:64-741 Crouch et al., J. Mol. Appl. Genet (1983) 2:273-283; and Simon et al., Plant Molecular Biology (1985) 5: 191-201, in which various forms of storage proteins in *Brassica napus* are described and by Beachy et al., EMBO. J. (1985) 4:3047-3053; Sengupta-Gopalan et al., Proc. Natl. Acad. Sci. USA (1985) 82:3320-3324; Greenwood and Chrispeels, Plant Physiol. (1985) 79:65-71 and Chen et al., Proc. Natl. Acad. Sci. USA (1986) 83:8560-8564, in which studies concerned with seed storage proteins and genetic manipulation are described and by Eckes et al., Mol. Gen. Genet. (1986) 205:14-22 and Fluhr et al., Science (1986) 232:1106-1112, in which genetic manipulation of light inducible plant genes are described.

There is now provided a DNA sequence of an expression cassette in which the potato tuber specific regulatory regions are localised and which contain a patatin-gene with a patatin-gene promoter.

The DNA sequence, that contains the regulatory transcriptional starter region having tuber specificity, can turn on a sequence, that contains the information for the modification of the phenotype of the concerning cell tissues and the formation both of quantitative distribution of endogenous products or the formation of heterogenous expression products for a new function. Conveniently, the transcription and termination regions in the direction of transcription should be provided by a linker or polylinker which contains one or more restriction positions for the insertion of this sequence. As a rule, the linker has 1-10, usually 1-8, preferably 2-6 restriction positions. In general the linker has a size of less than 100 bp, usually less than 60 bp, but is however at least 5 bp. The transcriptional starter region can be native, homologous to the host or foreign, heterologous, to the host plants. Of special interest are the transcriptional starter regions which are associated with potatoes (*Solanum tuberosum*) proteinase-inhibitor II-gene, that are expressed during the total potato tuber development from the formation of the stolon up to the ripe tuber. The transcription cassette contains in the 5'-3' transcription direction, a region representative for the plants, transcription and translation, a desired sequence and a region for transcriptional and translational termination. The termination region is optionally exchangeable.

The DNA sequence could contain all possible open reading frames for a desired peptide as well as also one or more introns. Examples include sequences for enzymes; sequences that are complementary (a) to a genome sequence whereby the genome sequence can be an open reading frame; (b) to an intron; (c) to a non-coding leading sequence; (d) to each sequence, which inhibits through complementarity, transcriptional mRNA processing (for example splicing) or translation. The desired DNA sequence can be synthetically produced or extracted naturally, or can contain a mixture of synthetic or natural DNA content. In general, a synthetic DNA sequence is produced, with condons which are preferred by the plants. These preferred codons from the plants can be specified from the codons with the highest protein frequency which can be expressed in the most interesting plant species. In the preparation of the transcription cassettes, the different DNA fragments can be manipulated in order to contain a DNA sequence, which leads generally in the correct direction and which is equipped with the correct reading frame. For the connections of the DNA fragments to each other, adaptors or linkers can be introduced on the fragment ends. Further manipulations can be introduced which provide the suitable restriction positions or separate the excess DNA or restriction positions. Where insertions, deletions or substitutions, such as for example transitions and transversions, are concerned, in vitro mutagenesis, primer repair, restriction or ligation can be used.

In suitable manipulations, such as for example restriction, "chewing-back" or filling up of overhangs for "blunt-ends", complementary ends of the fragments for the fusing and ligation could be used. To carry out the various steps which serve to ensure the expected success of the invention, cloning is necessary to increase the amount of DNA and for DNA analysis.

Many cloning vectors are available which contain a replication system for *E. coli* and a marker which allows for selection of the transformed cells. The vectors contain for example pBR 332, pUC series, M13 mp series, pACYC 184 etc. In such a way, the sequence can be introduced into a suitable restriction position in the vector. The contained plasmid is used for the transformation in *E. coli*. The *E. coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each plasmid sequence can be cloned in the same or different plasmid. After each method of introducing the desired gene in the plants, additional DNA sequences may be necessary. If for example, the Ti- or Ri-plasmid of the plant cells is used for the transformation, at least the right boundary and often the right and the left boundary of the Ti- and Ri-plasmid T-DNA, as flanking areas of the introduced gene, can be connected. The use of T-DNA for the transformation of plant cells is being intensively studied and is well described in EP 120 516; Hoekema, in: The Binary Plant Vector System Offset-drukkerij Kanters B. B., Alblasserdam, 1985, Chapter V; Fraley, at al., Crit. Rev. Plant Sci., 4:1–46 und An et al., EMBO J. (1985) 4:277–284.

When the introduced DNA is first integrated into the genome, it is then also relatively stable and as a rule does not comes out anymore. It normally contains a selection marker which passes on to the transformed plant cells, resistance against a biocide or an antibiotic such as kanamycin, G 418, bleomycin, hygromycin or chloramphenicol, among others. The particular marker employed should be one which will allow for selection of transformed cells compared to cells lacking the marker DNA which has been introduced.

A variety of techniques are available for introduction of DNA into a plant host cell. These techniques include transformation with T-DNA using *Agrobacterium tumefaciens* or *Agrobacterium rhizogenes* as transformation agent, fusion, injection, or electroporation, as well as further possibilities. If Agrobacteria are used for transformation, the introduced DNA must be cloned in special plasmid and either in an intermediary vector or a binary vector. The intermediary vectors which are based on sequences which are homologous with sequences in the T-DNA can be integrated through homologous recombination in the Ti- or Ri- plasmid. These also contain the necessary Vir-region for the transfer of the T-DNA. Intermediary vectors cannot be replicated in Agrobacteria. By means of helper-plasmid, the intermediary vector of *Agrobacterium tumefaciens* can be transferred (conjugation). Binary vectors can be replicated in *E. coli* as well as in Agrobacteria. They contain a selection marker gene and a linker or polylinker, which are framed from the right and left T-DNA border regions. They can be transformed directly in the agrobacteria (Holsters et al., Mol. Gen. Genet.(1978) 163: 181–187). The Agrobacterium serving as host cells should contain a plasmid that carries the Vir-region, which is necessary for the transfer of the T-DNA in the plant cells whereby additional T-DNA can be contained. The bacterium so transformed is used for the transformation of plant cells. For the transfer of DNA in the plant cells, plant explanates can be cultivated in suitable manner with *Agrobacterium tumefaciens* or *Agrobacterium rhizogenes*. From the infected plant material (for example leaf bits, stem segments, roots as well as protoplasts or suspensions of cultivated cells), whole plants can then be regenerated in a suitable medium which can contain antibiotics or biocides for selection, which then can be tested for the presence of introduced DNA. With injection and electroporation methods, no special requirements on the plasmid are needed and a simple plasmid, for example pUC derivative can be used.

For the introduction of foreign genes into plants there are many possibilities, but of especial interest is the expression of genes for mammalian products such as for example blood factors; lymphokines; colony stimulation factors; interferons; plasminogen activators, enzymes such as for example superoxide dismutase or chymosin; hormone; thioesterase-2 from rat milk or human serum albumin. A further possibility is increasing the amounts of tuber proteins, especially mutated tuber proteins, which have optimised amino acid composition (essential amino acids) and in this way increase the nutritive value of the tubers. Should the amounts of specified endogenous products be reduced, the expression of the gene or parts of this gene in the wrong orientation to the promoter is also conceivable, leading to the synthesis of an RNA, which is complementary to a total or to parts of an endogenous gene and thus the transcription of this gene or the processing and/or translation of the endogenous mRNA can be inhibited.

The transformed cells grow within the plants in the usual way (see also McCormick et al., Plant Cell Reports (1986) 5, 81–84). These plants can be grown normally and crossed with plants, that possess the same transformed gene or other genes. The resulting hybridised individuals have the corresponding phenotypic properties. Two or more generations should be grown, in order to secure that the phenotypic state remains stable and will be passed on, especially if seeds are to be harvested, in order to ensure that the corresponding phenotype or other individual characteristics are included. Suitable as host plants for the potato specific expression are all species or tuber forming plant species especially *Solanum tuberosum*.

The identification of necessary transcriptional starting regions can be achieved in a number of ways. There can be used as a rule mRNAs that are isolated from specific parts of plants (tubers). For additional increase in the concentration of the mRNA specific to the cells or associated with plant conditions, cDNA can be prepared whereby non-specific cDNA from the mRNA or the cDNA from other tissues or plant conditions (for example wounded/non-wounded) can be drawn off. The remaining cDNA can then be used for probing the genome for complementary sequences using a suitable plant DNA library. Where the protein is to be isolated, it can be partially sequenced so that a probe for direct identification of the corresponding sequences in a plant DNA library can be produced. The sequences that are hybridised with the probe can then be isolated and manipulated. Further, the non-translated 5'-region, that is associated with the coded area, can be isolated and used in expression cassettes for the identification of the transcriptional activity of the non-translated 5'-regions.

The expression cassette obtained, which the non-translated 5'-region uses, can be transformed in plants (see above) in order to test their functionability with a heterologous structure (other than the open reading frame of wild types which is associated with the non-translated 5'-region) as well as the tuber specificity. In this way specific sequences that are not necessary for the tuber specific transcription can be identified. Expression cassettes that are of special interest contain transcriptional initiation positions of the patatin gene.

Expressions & Abbreviations
Abbreviations:
d, kd=Dalton, kilodalton
bp=Base pairs
cDNA=A copy of a mRNA produced by reverse transcriptase.
mRNA=Messenger ribonucleic acid.
T-DNA=Transfer-DNA (localised on the Ti-plasmid from *Agrobacterium tumefaciens*)
Terms:
Blunt ends=DNA ends in which both DNA strands are exactly the same length.
Chewing-back=Enzymatic removal of nucleotides of a DNA strand which is longer than the complementary strand of a DNA molecule.
Electrophoresis=A biochemical process of separation for separating nucleic acids from proteins according to size and charge.
Expression=Activity of a gene.
Gene=Genetic factor; a unit of inheritance, carrier of at least part of the information for a particular specified characteristic. Genes consist of nucleic acids (eg DNA, RNA).
Genome=Totality of the genes localised in the chromosomes of the cell.
Genome-sequence=The DNA sequence of the genome whereby three nucleotide bases lying within it form a codon which code again for a specific amino acid.
RNA splicing=A gene does not always show up as a colinear unity but can contain non-coded sequences (introns) which must be spliced from the mRNA (splicing).
Heterologous gene(s) or DNA=Foreign genes or foreign DNA.
Homologous gene(s) or DNA=Gene or DNA derived from the same species.
Clone=Cell population that is derived from one of its own mother cells. Descendants are genotypically the same. By cloning, the homogeneity of cell lines can be increased further.
Ligation=Enzymatic formation of a phosphodiester bond between 5'-phosphate groups and 3'-hydroxy groups of the DNA.
Linker, Polylinker=Synthetic DNA sequence that contains one or more (polylinker) restriction cutting regions in direct sequence.
Northern blots,=Transfer and fixing of
Southern blots, electrophoretically separate RNA or DNA on a nitrocellulose or nylon membrane.
Patatin=Trivial name for main storage protein of potato tubers; a glycoprotein of ca. 40 kd molecular weight.
Phenotype=A sum of the characteristics, which are expressed in an organism as opposed to its genotype.

Plasmid=Additional extrachromosomal DNA gene carrier in bacteria cells (possibly also in eukaryons) which reduplicate themselves independently of the bacterial chromosomes. The plasmid can be integrated in other DNA hosts.

Primer=Starting piece; polynucleotide strand on which further nucleotides can be attached.

Promoter=Control sequence of DNA expression which realises the transcription of homologous or heterologous DNA gene sequences.

Replication=Doubling of the DNA sequence.

Restriction enzymes=Restriction endonucleases that result in particular sub-units of endo DNA's (for example EcoRI (specificity G↓AATTC and EcoRII↓CC ($^A_T$) GG from *E. coli*); characterized by high specificity of the substrate (↓=splitting position).

Restriction positions=A splitting position which is produced specifically by restriction enzymes.

Termination=A last stage of the protein and/or the RNA synthesis.

Transformation=Introduction of exogenous DNA of a bacterial species into receiver cell.

Transcription=Overwriting on an RNA the genetic information contained in the DNA.

Translation=Translation of the genetic information which is memorised in the form of a linear sequence of bases in nucleic acids. The product of the translation is a polypeptide that comprises a sequence of amino acids.

Transition=Base pair exchange: purine-pyrimidine to purine-pyrimidine e.g. A-T exchanging G-C.

Transversion=Base pair exchange: purine-pyrimidine to pyrimidine-purine e.g. A-T replacing T-A.

Deletion=Removal of one or more base pairs;

Insertion=Introduction of one or more base pairs; Transition, Transversion, Deletion and Insertion are point mutations.

Vectors=Host specific replicatable structures, that take up genes and carry these into other cells. Plasmid can also be used as vectors.

On 16.12.1988 the following microorganism was deposited at the German Collection for Microorganisms (DSM) in Braunschweig, Germany (deposit number):

*Agrobacterium tumefaciens* LBA4404, A. tum. M 14, containing the plasmid pBI 101-B33 (DSM 5089)

DESCRIPTION OF THE FIGURES

FIG. 2 shows the nucleic acid sequence for the transcriptional regulation of important areas of the patatin-gene. In the sequence, the position of the DraI/DraI fragments between position +14 and position −1513, eg by Pfeil, is marked. ATG indicates the start of the translation (shown by ▼).

DETAILED DESCRIPTION OF THE INVENTION

Figure 1:
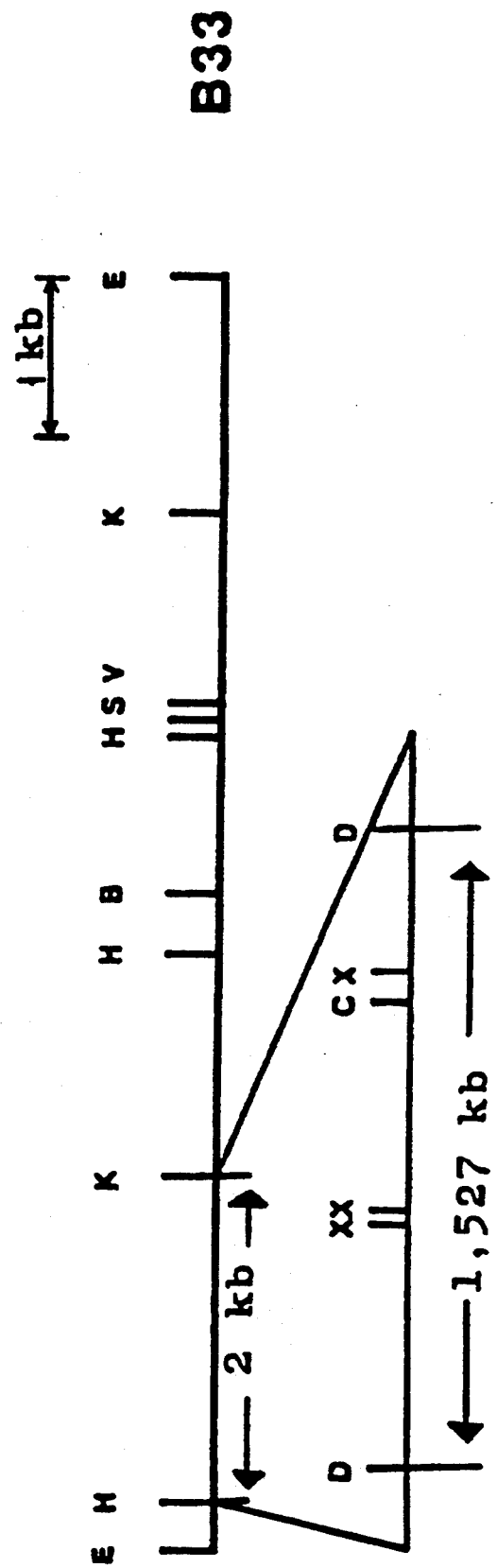
FIG. 1 shows the restriction map of the genomic clone that codes the potato gene B33
Abbreviations:
E=Eco RI, H=HindIII, K=KpnI, B=Bam HI, S=SstI, V=Eco RV, X=XbaI, C=ClaI, D=DraI

For a better understanding of this invention the following examples are given. An explanation for these experiments is given as follows:

1. Cloning Vectors

For cloning, the vectors pUC18/19 (Yanisch-Perron et al Gene (1985), 33, 103–119) were used.

For plant transformations, the gene structures were cloned in the binary vector BIN19 (Bevan, Nucl Acids Research (1984), 12, 8711–8720).

2. Bacterial Species

For the pUC-and M13 vectors the *E. coli* species BMH71-18 (Messing et al, Proc. Nat. Acad. Sci. USA (1977), 24, 6342–6346) or TB1 was used. For the vectors pMPK110 and BIN19, the species TB1 was exclusively used. TB1 is a recombinant, negative, tetracyclines resistant derivative of the species JM101 (Yanisch-Perron et al., Gene (1985), 33, 103–119). The genotype of the TB1 species is (Bart Barrel, personal communication): F'(traD36, proAB, lacI, lacZΔM15), Δ(lac, pro), SupE, thiS, recA, Sr1::Tn10(Tc$^R$).

The plant transformation was carried out with the help of the *Agrobacterium tumefaciens* species LBA4404 (Bevan, M., Nucl. Acids Res. 12, 8711–8721 (1984); Bin19-derivative).

Medium

YT-Medium: 0.5% Yeast extract, 0.5% NaCl; 0.8% bacto-trypton, if necessary in 1.5% agar.

YEB-Medium: 0.5% beef extract, 0.1% yeast extract, 0.5% peptone, 0.5% saccharose, 2 mM MgSO$_4$, if necessary in 1.5% agar.

MS-Medium: According to Murashige and Skoog (Physiologia Plantarum (1962), 15, 473–497).

3. Transformation of *Agrobacterium tumefaciens*.

The introduction of the DNA in the Agrobacterium in RIN-19-derivatives is carried out by direct transformation by the method of Holsters et al (Mol. Gen. Genet. (1978), 163, 181–187). The plasmid DNA from transformed agrobacteria are isolated by the method of Birnboim and Doly (Nucl. Acids Res. (1979), 7, 1513–1523) and separated by gel electrophoresis after suitable restriction cleavage.

4. Plant Transformation 10 small leaves of a sterile potato culture, wounded with a scalpel, were put into 10 ml MS-medium with 2% saccharose which contained 30 to 50 μl of an overnight culture of *Agrobacterium tumefaciens*, washed under selection. After 3–5 minutes gentle shaking, the petri dishes were incubated at 25° C. in the dark. After two days, the leaves were laid in MS-medium with 1.6% glucose, 2 mg/l zeatinribose, 0.02 mg/l naphthylacetic acid, 0.02 mg/l gibberellic acid, 500 mg/l claforan, 50 mg/l kanamycin and 0.8% bactoagar. After one week incubation at 25° C. and 3000 lux the claforan concentration in the medium was reduced by half.

5. Analysis of the Genomic DNA from Transgenic Plants

The isolation of genomic plant DNA was carried out by the method of Rogers and Bendich (Plant Mol. Biol (1985), 5, 69–76).

For DNA analysis 10–20 μg DNA was tested after suitable restriction cleavage with the aid of Southern blots to determine the integration of the DNA sequences being analysed.

6. Analysis of the Total RNA from Transgenic Plants

The isolation of the total plant RNA was carried out by the method of Longemann et al (Analytical Biochem (1987), 163, 16–20).

For the analysis, 50 μg samples of total RNA were tested with the use of Northern blots to determine the presence of the sought transcripts.

7. GUS-Test

The activity of the β-glucuronidase (GUS) in transgenic plants was determined by the method of Jefferson (Plant Mol. Biol. Rep. (1987), 5, 387–405). The protein determination was carried out by the method of Bradford (Anal. Biochem. (1976), 72, 248–254). For the determination of the gus activity, 50 μg protein was used, and incubation was carried out at 37° C. for 30 minutes.

The following examples illustrate the isolation and identification as well as the function and use of patatin promoters in potato tubers.

EXAMPLE 1

Cloning and structural analysis of a patatin gene from *Solanum tuberosum*.

cDNA clones that code for the patatin protein in potatoes, were isolated and sequenced from the potato variety Berolina (Rosahl et al Mol. Gen. Genetics 203, 214–220 (1986). These cDNA clones then served to isolate a homologous genomic patatin clone from the potato variety Berolina (Max-Planck-Instut für Zuchtungsforschung, Köln).

EXAMPLE 2

Cloning, identification and primary structure of a genomic patatin clone.

A genomic library of the nuclear DNA from the potato variety Berolina which was established in the vector from lambda phages EMBL 4, was screened using the patatin cDNA pcT 58. Thirteen independent clones were obtained which were used for the further work after partial sequencing of the clone B33. The restriction map of the clone B33 is shown in FIG. 1. Part of the gene was sequenced, the sequence of the important areas for the transcriptional regulation is given in FIG. 2.

EXAMPLE 3

Identification of the regulatory regions responsible for the specific expression of the patatin gene B33.

Figure 3:
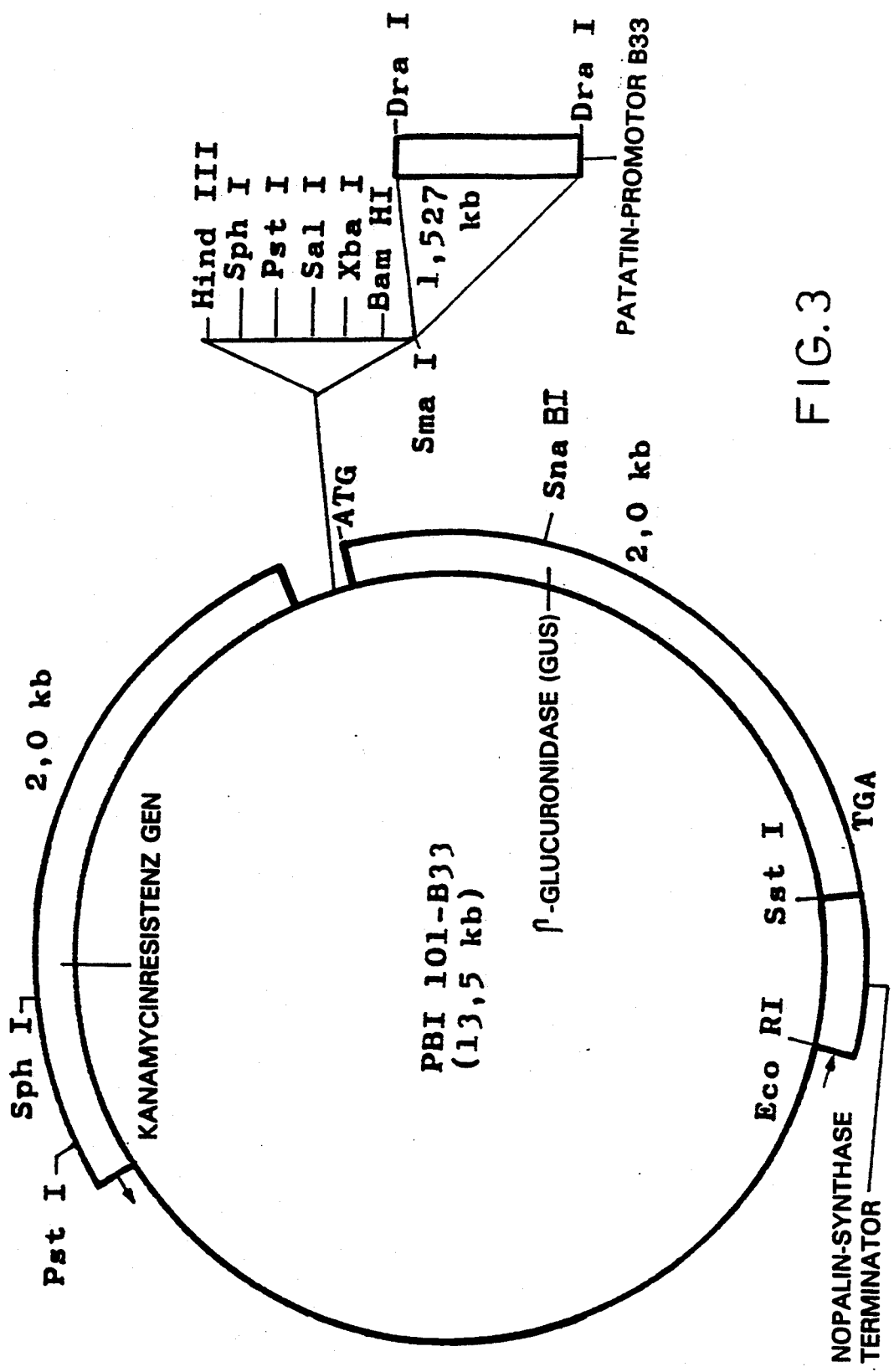
FIG. 3 shows the 13.5 kb long plasmid PBI101-B33, with the 2.0.kb long kanamycin resistance gene, the 1.527 kb long patatin-promoter B 33, the 2.0.kb long β-glucuronidase resistance gene and the nopaline synthase terminator, contained within it.

A 1.527 kb long DraI/DraI fragment which is located between position +14 and position -1513 (see FIG. 2) was inserted in the SmaI cutting position of the plasmid pBO101 (Jefferson et al, EMBO J. 6, 3901-3907 (1987). In this way these promoter fragments of the patatin gene B33 with the coded region of the β-glucuronidase from *E. coli* and the poly-A containing region of the nopaline synthase gene were fused (see FIG. 3). The fusion of the nopaline synthase terminator takes place on the poly A containing region of the terminator. These construction were transferred into the *Agrobacterium species* LBA 4404 (Bevan, M., Nucl. Acids Res. 12, 8711–8721 (1984) and the agrobacteria containing the chimeric patatin gene was used for transformation of potato leaves.

From ten independent containing transformants, in which the presence of the intact non-rearranged chimeric patatin glucuronidase gene was demonstrated, using Southern blot analyses, leaves, stems, tubers and roots were analysed for activity of the β-glucuronidase.

The results are shown in Table 1. From these data it will be seen that the DraI/DraI fragment of the patatin gene B33 which was fused with the β-glucuronidase gene has a strong potato specific activity of the β-glucuronidase.

TABLE 1

Glucuronidase of the chimeric B33 glucuronidase gene in various organs of different transgenic potato plants.

| Transformant | Root | Stem | Leaf | Tuber |
|---|---|---|---|---|
| 33G-12 | 137 | 55 | 0 | 16882 |
| 33G-19 | 138 | 7 | 14 | 2047 |
| 33G-21 | 155 | 1034 | 25 | 19471 |
| 33G-23 | 0 | 50 | 0 | 12149 |
| 33G-24 | 0 | 14 | 0 | 4530 |
| 33G-27 | 86 | 8 | 4 | 7284 |
| 33G-38 | 30 | 14 | 6 | 3847 |
| 33G-52 | 69 | 10 | 0 | 2864 |
| 33G-61 | 31 | 10 | 2 | 14916 |
| 33G-62 | 133 | 151 | 24 | 18620 |
| x | 76 | 135 | 7.5 | 11948 |
| c.v. Desiree | 0 | 0 | 1 | 0 |

Activities are given in pMol methylumbelliferrol/mg protein/minute c.v. Desiree shows corresponding activity in an untransformed potato plant

|      |            |            |            |            |            |
|------|------------|------------|------------|------------|------------|
| 1    | TTTAAATCAT | TGTTTTATTT | TCTCTTTCTT | TTTACAGGTA | TAAAAGGTGA |
| 51   | AAATTGAAGC | AAGATTGATT | GCAAGCTATG | TGTCACCACG | TTATTGATAC |
| 101  | TTTGGAAGAA | ATTTTTACTT | ATATGTCTTT | GTTTAGGAGT | AATATTTGAT |
| 151  | ATGTTTTAGT | TAGATTTTCT | TGTCATTTAT | GCTTTAGTAT | AATTTTAGTT |
| 201  | ATTTTTATTA | TATGATCATG | GGTGAATTTT | GATACAAATA | TTTTTGTCAT |
| 251  | TAAATAAATT | AATTTATCAC | AACTTGATTA | CTTTCAGTGA | CAAAAAATGT |
| 301  | ATTGTCGTAG | TACCCTTTTT | TGTTGAATAT | GAATAATTTT | TTTTATTTTG |
| 351  | TGACAATTGT | AATTGTCACT | ACTTATGATA | ATATTTAGTG | ACATATATGT |
| 401  | CGTCGGTAAA | AGCAAACACT | TTCAGTGACA | AAATAATAGA | TTTAATCACA |
| 451  | AAATTATTAA | CCTTTTTTAT | AATAATAAAT | TTATCCCTAA | TTTATACATT |
| 501  | TAAGGACAAA | GTATTTTTTT | TATATATAAA | AAATAGTCTT | TAGTGACGAT |
| 551  | CGTAGTGTTG | AGTCTAGAAA | TCATAATGTT | GAATCTAGAA | AAATCTCATG |
| 601  | CAGTGTAAAA | TAAACCTCAA | AAAGGACGTT | CAGTCCATAG | AGGGGGTGTA |
| 651  | TGTGACACCC | CAACCTCAGC | AAAAGAAAAC | CTCCCTTCAA | CAAGGACATT |
| 701  | TGCGGTGCTA | AACAATTTCA | AGTCTCATCA | CACATATATT | TATTATATAA |
| 751  | TACTAATAAA | GAATAGAAAA | GGAAAGGTAA | ACATCATTAA | ATCGTCTTTG |
| 801  | TATATTTTTA | GTGACAACTG | ATTGACGAAA | TCTTTTTCGT | CACACAAAAT |
| 851  | TTTTAGTGAC | GAAACATGAT | TTATAGATGA | TGAAATTATT | TGTCCCTCAT |
| 901  | AATCTAATTT | GTTGTAGTGA | TCATTACTCC | TTTGTTTGTT | TTATTTGTCA |
| 951  | TGTTAGTCCA | TTAAAAAAAA | ATATCTCTCT | TCTTATGTAC | GTGAATGGTT |
| 1001 | GGAACGGATC | TATTATATAA | TACTAATAAA | GAATAGAAAA | AGGAAAGTGA |
| 1051 | GTGAGGTTCG | AGGGAGAGAA | TCTGTTTAAT | ATCAGAGTCG | ATCATGTGTC |
| 1101 | AATTTTATCG | ATATGACCCT | AACTTCAACT | GAGTTTAACC | AATTCCGATA |
| 1151 | AGGCGAGAAA | TATCATAGTA | TTGAGTCTAG | AAAAATCTCA | TGTAGTGTGG |
| 1201 | GGTAAACCTC | AGCAAGGACG | TTGAGTCCAT | AGAGGGGGGT | GTATGTGACA |
| 1251 | CCCCAACCTC | AGCAAAAGAA | AACCTCCCCT | CAAGAAGGAC | ATTTGCGGTG |
| 1301 | CTAAACAATT | TCAAGTCTCA | TCACACATAT | ATATATATTA | TATAATACTA |
| 1351 | ATAAATAATA | GAAAAAGGAA | AGGTAAACAT | CACTAACGAC | AGTTGCGGTG |
| 1401 | CAAACTGAGT | GAGGTAATAA | ACAGCACTAA | CTTTTATTGG | TTATGTCAAA |
| 1451 | CTCAAAGTAA | AATTTCTCAA | CTTGTTTACG | TGCCTATATA | TACCATGCTT |
| 1501 | GTTATATGCT | CAAAGCACCA | ACAAAATTT. |            |            |

We claim:

1. A process for the production of transgenic potato plants, characterized in that the transgenic potato plants express a DNA sequence of heterologous origin specifically in their tubers, comprising the following steps:
   a) producing an expression cassette having the following sequences:
      i) a B33 promoter sequence of a patatin gene derived from *Solanum tuberosum*, and which leads to a tuber specific expression of sequences fused to the B33 promoter sequence,
      ii) a DNA sequence of heterologous origin, which is fused in sense orientation to the B33 promoter sequence, and
      iii) a DNA sequence for transcriptional and translational termination;
   b) transferring the expression cassette into potato cells thereby producing transformed potato cells; and
   c) regenerating whole, intact transgenic potato plants from the transformed potato cells, wherein the transgenic potato plants express the DNA sequence of heterologous origin specifically in their tubers.

2. The process according to claim 1, wherein the expression cassette is transferred into potato cells using recombinant plasmids.

3. A process according to claim 1, wherein the B33 patatin promoter sequence has a DNA sequence consisting of:

4. A process for the production of transgenic potato plants, characterized in that the transgenic potato plants express a DNA sequence of heterologous origin specifically in their tubers, comprising the following steps:
   a) producing an expression cassette having the following sequences:
      i) a B33 promoter sequence of a patatin gene derived from *Solanum tuberosum*, which is the DraI/DraI fragment located between position +14 and position −1513 of the KpnI/Hind III sequence shown in FIG. 2 and which leads to a tuber specific expression of sequences fused to the B33 promoter sequence,
      ii) a DNA sequence of heterologous origin, which is fused in sense orientation to the B33 promoter sequence, and
      iii) a DNA sequence for transcriptional and translational termination;
   b) transferring the expression cassette into potato cells thereby producing transformed potato cells; and
   c) regenerating whole, intact transgenic potato plants from the transformed potato cells, wherein the transgenic potato plants express the DNA sequence of heterologous origin at a level at least 100 higher in their tubers than in their roots, stems, or leaves.

5. The process according to claim 4, wherein the expression cassette is transferred into potato cells using recombinant plasmids.

6. A transgenic potato plant containing an expression cassette having the following sequences:
i) a B33 promoter sequence of a patatin gene derived from *Solanum tuberosum*, and which leads to a tuber specific expression of sequences fused to the B33 promoter sequence,
ii) a DNA sequence of heterologous origin, which is fused in sense orientation to the B33 promoter sequence, and
iii) a DNA sequence for transcriptional and translational termination, wherein the transgenic potato plant expresses the DNA sequence of heterologous origin at a level at least 100 higher in its tubers than in its roots, stems, or leaves.

7. A trangenic potato plant according to claim 6, wherein the patatin promoter sequence has a DNA sequence consisting of:

| | | | | | |
|---|---|---|---|---|---|
| 1 | TTTAAATCAT | TGTTTTATTT | TCTCTTTCTT | TTTACAGGTA | TAAAAGGTGA |
| 51 | AAATTGAAGC | AAGATTGATT | GCAAGCTATG | TGTCACCACG | TTATTGATAC |
| 101 | TTTGGAAGAA | ATTTTTACTT | ATATGTCTTT | GTTTAGGAGT | AATATTTGAT |
| 151 | ATGTTTTAGT | TAGATTTTCT | TGTCATTTAT | GCTTTAGTAT | AATTTTAGTT |
| 201 | ATTTTTATTA | TATGATCATG | GGTGAATTTT | GATACAAATA | TTTTTGTCAT |
| 251 | TAAATAAATT | AATTTATCAC | AACTTGATTA | CTTTCAGTGA | CAAAAAATGT |
| 301 | ATTGTCGTAG | TACCCTTTTT | TGTTGAATAT | GAATAATTTT | TTTTATTTTG |
| 351 | TGACAATTGT | AATTGTCACT | ACTTATGATA | ATATTTAGTG | ACATATATGT |
| 401 | CGTCGGTAAA | AGCAAACACT | TTCAGTGACA | AAATAATAGA | TTTAATCACA |
| 451 | AAATTATTAA | CCTTTTTTAT | AATAATAAAT | TTATCCCTAA | TTTATACATT |
| 501 | TAAGGACAAA | GTATTTTTTT | TATATATAAA | AAATAGTCTT | TAGTGACGAT |
| 551 | CGTAGTGTTG | AGTCTAGAAA | TCATAATGTT | GAATCTAGAA | AAATCTCATG |
| 601 | CAGTGTAAAA | TAAACCTCAA | AAAGGACGTT | CAGTCCATAG | AGGGGGTGTA |
| 651 | TGTGACACCC | CAACCTCAGC | AAAAGAAAAC | CTCCCTTCAA | CAAGGACATT |
| 701 | TGCGGTGCTA | AACAATTTCA | AGTCTCATCA | CACATATATT | TATTATATAA |
| 751 | TACTAATAAA | GAATAGAAAA | GGAAAGGTAA | ACATCATTAA | ATCGTCTTTG |
| 801 | TATATTTTTA | GTGACAACTG | ATTGACGAAA | TCTTTTTCGT | CACACAAAAT |
| 851 | TTTTAGTGAC | GAAACATGAT | TTATAGATGA | TGAAATTATT | TGTCCCTCAT |
| 901 | AATCTAATTT | GTTGTAGTGA | TCATTACTCC | TTTGTTTGTT | TTATTTGTCA |
| 951 | TGTTAGTCCA | TTAAAAAAAA | ATATCTCTCT | TCTTATGTAC | GTGAATGGTT |
| 1001 | GGAACGGATC | TATTATATAA | TACTAATAAA | GAATAGAAAA | AGGAAAGTGA |
| 1051 | GTGAGGTTCG | AGGGAGAGAA | TCTGTTTAAT | ATCAGAGTCG | ATCATGTGTC |
| 1101 | AATTTTATCG | ATATGACCCT | AACTTCAACT | GAGTTTAACC | AATTCCGATA |
| 1151 | AGGCAGAAAA | TATCATAGTA | TTGAGTCTAG | AAAAATCTCA | TGTAGTGTGG |
| 1201 | GGTAAACCTC | AGCAAGGACG | TTGAGTCCAT | AGAGGGGGGT | GTATGTGACA |
| 1251 | CCCCAACCTC | AGCAAAAGAA | AACCTCCCCT | CAAGAAGGAC | ATTTGCGGTG |
| 1301 | CTAAACAATT | TCAAGTCTCA | TCACACATAT | ATATATATTA | TATAATACTA |
| 1351 | ATAAATAATA | GAAAAAGGAA | AGGTAAACAT | CACTAACGAC | AGTTGCGGTG |
| 1401 | CAAACTGAGT | GAGGTAATAA | ACAGCACTAA | CTTTTATTGG | TTATGTCAAA |
| 1451 | CTCAAAGTAA | AATTTCTCAA | CTTGTTTACG | TGCCTATATA | TACCATGCTT |
| 1501 | GTTATATGCT | CAAAGCACCA | ACAAAATTT. | | |

* * * * *